(12) United States Patent
Park et al.

(10) Patent No.: US 10,874,378 B2
(45) Date of Patent: Dec. 29, 2020

(54) WIRELESS PROBE, ULTRASOUND DIAGNOSTIC APPARATUS, AND METHOD OF CONTROLLING WIRELESS PROBE AND ULTRASOUND DIAGNOSTIC APPARATUS

(71) Applicant: SAMSUNG MEDISON CO., LTD., Gangwon-do (KR)

(72) Inventors: Hyun Park, Seoul (KR); Sun-Mo Yang, Hwaseong-si (KR); Gil-Ju Jin, Seoul (KR)

(73) Assignee: SAMSUNG MEDISON CO., LTD., Gangwon-do (KR)

( * ) Notice: Subject to any disclaimer, the term of this patent is extended or adjusted under 35 U.S.C. 154(b) by 1122 days.

(21) Appl. No.: 14/726,339

(22) Filed: May 29, 2015

(65) Prior Publication Data
US 2016/0135791 A1    May 19, 2016

(30) Foreign Application Priority Data
Nov. 13, 2014   (KR) ........................ 10-2014-0157963

(51) Int. Cl.
*A61B 8/00* (2006.01)
*H04W 8/22* (2009.01)
*G06F 11/14* (2006.01)

(52) U.S. Cl.
CPC .............. *A61B 8/54* (2013.01); *A61B 8/4405* (2013.01); *A61B 8/4438* (2013.01); *A61B 8/4472* (2013.01); *A61B 8/466* (2013.01); *G06F 11/1451* (2013.01); *G06F 11/1469* (2013.01); *H04W 8/22* (2013.01); *A61B 8/465* (2013.01)

(58) Field of Classification Search
CPC ......... A61B 8/54; A61B 8/466; A61B 8/4438; A61B 8/4405; A61B 8/4472; A61B 8/465; G06F 11/1451; G06F 11/1469; H04W 8/22
See application file for complete search history.

(56) References Cited

U.S. PATENT DOCUMENTS

| 6,527,719 B1 | 3/2003 | Olsson et al. | |
| 9,218,452 B2* | 12/2015 | Varna | G16H 10/60 |
| 2004/0181154 A1* | 9/2004 | Peterson | A61B 8/00 600/459 |
| 2006/0049957 A1* | 3/2006 | Surgenor | G06F 19/00 340/4.1 |
| 2007/0219480 A1* | 9/2007 | Kamen | G05D 7/0647 604/20 |
| 2008/0208051 A1 | 8/2008 | Choi | |
| 2009/0043203 A1 | 2/2009 | Pelissier et al. | |

(Continued)

FOREIGN PATENT DOCUMENTS

| JP | 5-253221 A | 10/1993 |
| JP | 2002-360568 A | 12/2002 |
| JP | 2012-143296 A | 8/2012 |

*Primary Examiner* — Peter Luong
(74) *Attorney, Agent, or Firm* — Morgan, Lewis & Bockius LLP

(57) ABSTRACT

Disclosed herein are a wireless probe, an ultrasound diagnostic apparatus, and a method of controlling the wireless probe and the ultrasound diagnostic apparatus. The wireless probe may include a power supply unit that supplies power to the wireless probe, and a controller that controls configuration information of the wireless probe to be backed up or restored based on a change in an operational state of the wireless probe.

14 Claims, 11 Drawing Sheets

(56) References Cited

U.S. PATENT DOCUMENTS

2010/0160786 A1    6/2010  Nordgren et al.
2011/0112399 A1    5/2011  Willems et al.
2014/0371592 A1*  12/2014  Yamamoto ............... A61B 8/14
                                                   600/443

\* cited by examiner

WIRELESS PROBE, ULTRASOUND DIAGNOSTIC APPARATUS, AND METHOD OF CONTROLLING WIRELESS PROBE AND ULTRASOUND DIAGNOSTIC APPARATUS

CROSS-REFERENCE TO RELATED APPLICATION

This application claims the benefit of Korean Patent Application No. 10-2014-0157963, filed on Nov. 13, 2014 in the Korean Intellectual Property Office, the disclosure of which is incorporated herein by reference.

BACKGROUND

1. Field

Embodiments of the present invention relate to a wireless probe for capturing an ultrasound diagnostic image, and an ultrasound diagnostic apparatus.

2. Description of the Related Art

An ultrasound diagnostic system is one of major diagnostic systems that have been applied in various fields, and has been widely used in a medical field since the ultrasound diagnostic system has noninvasive and nondestructive characteristics. The ultrasound diagnostic system obtains a diagnostic image of the inside of an object using a probe and two or three-dimensionally displays the diagnostic image using an ultrasound diagnostic apparatus.

Recently, wireless probes that can be wirelessly connected to an ultrasound diagnostic apparatus and that include an additional independent power supply device to increase user convenience have been widely used.

SUMMARY

In accordance with one aspect of the present invention, a wireless probe includes a power supply unit that supplies power to the wireless probe; and a controller that controls configuration information of the wireless probe to be backed up or restored, based on a change in an operational state of the wireless probe.

In a case in which the operational state of the wireless probe changes from a normal state to an abnormal state, the controller may back up the configuration information of the wireless probe in a memory unit, wherein an ultrasound diagnostic image is capturable in the normal state and cannot be captured in the abnormal state.

In a case in which the operational state of the wireless probe changes from the abnormal state to the normal state, the controller may restore configuration of the wireless probe, based on the configuration information of the wireless probe that is backed up in the memory unit.

The case in which the operational state of the wireless probe changes from the normal state to the abnormal state may include at least one of a case in which the power supply unit is detached from the wireless probe; a case in which the power supply unit is discharged; a case in which the wireless probe enters a maximum power save mode; and a case in which the wireless probe enters an operation stop mode in which use of the wireless probe is stopped by a user.

The wireless probe may further include a communication unit that supports wireless communication to be established between the wireless probe and an ultrasound diagnostic apparatus.

The configuration information of the wireless probe may include at least one selected from the group consisting of gain information, zoom information, focus information, time gain compensation (TGC) information, depth information, frequency information, power information, frame average information, and dynamic range information of the wireless probe.

The configuration information of the wireless probe may include identification information identifying an ultrasound diagnostic apparatus connected to the wireless probe via a wireless communication network.

The controller may determine whether the configuration information of the wireless probe is backed up normally in the memory unit.

The controller may determine whether the configuration of the wireless probe is restored based on the configuration information of the wireless probe that is backed up in the memory unit.

The wireless probe may further include a display that displays at least one of information regarding the operational state of the wireless probe; information regarding a backed up state of the configuration information of the wireless probe; and information regarding a restored state of the configuration information of the wireless probe.

The wireless probe may further include a speaker that outputs at least one of information regarding the operational state of the wireless probe; information regarding a backed up state of the configuration information of the wireless probe; and information regarding a restored state of the configuration information of the wireless probe.

The wireless probe may further include a light-emitting display device that displays at least one of information regarding the operational state of the wireless probe; information regarding a backed up state of the configuration information of the wireless probe; and information regarding a restored state of the configuration information of the wireless probe.

In accordance with another aspect of the present invention, a ultrasound diagnostic apparatus includes a communication unit to support wireless communication to be established between the ultrasound diagnostic apparatus and a wireless probe; and an interface unit to receive a control command related to a back operation or a restoration operation for the wireless probe, based on information regarding an operational state of the wireless probe received through the wireless communication.

When the operational state of the wireless probe changes, the communication unit may receive the information regarding the operational state of the wireless probe from the wireless probe through the wireless communication.

The interface unit may provide a backed up state of configuration information of the wireless probe.

The interface unit may display, on a display, at least one of information regarding the operational state of the wireless probe; information regarding a backed up state of the configuration information of the wireless probe; and information regarding a restored state of the configuration information of the wireless probe.

The interface unit may output, via a speaker, at least one of information regarding the operational state of the wireless probe; information regarding a backed up state of the configuration information of the wireless probe; and information regarding a restored state of the configuration information of the wireless probe.

The interface unit may display, via a light-emitting display device, at least one of information regarding the operational state of the wireless probe; information regarding a backed up state of the configuration information of the wireless probe; and information regarding a restored state of the configuration information of the wireless probe.

In accordance with another aspect of the present invention, a method of controlling a wireless probe includes determining a change in an operational state of the wireless probe; and controlling configuration information of the wireless probe to be backed up or restored, based on the change in the operational state of the wireless probe.

The determining of the change in the operational state of the wireless probe may include determining whether the wireless probe changes from a normal state to an abnormal state or changes from the abnormal state to the normal state, wherein an ultrasound diagnostic image is capturable in the normal state and cannot be captured in the abnormal state.

The controlling of the configuration information of the wireless probe may include backing up the configuration information of the wireless probe in a memory unit when it is determined that the operational state of the wireless probe changes from the normal state to the abnormal state.

The controlling of the configuration information of the wireless probe may include restoring configuration of the wireless probe based on the configuration information of the wireless probe that is backed up in the memory unit, when it is determined that the operational state of the wireless probe changes from the abnormal state to the normal state.

The configuration information of the wireless probe may include at least one selected from the group consisting of gain information, zoom information, focus information, time gain compensation (TGC) information, depth information, and dynamic range information of the wireless probe.

The configuration information of the wireless probe may include identification information identifying an ultrasound diagnostic apparatus establishing wireless communication with the wireless probe.

In accordance with another aspect of the present invention, a method of controlling an ultrasound diagnostic apparatus includes receiving information regarding an operational state of a wireless probe; receiving a control command related to a backup operation or a restoration operation for the wireless probe based on the information regarding the operational state of the wireless probe; and transmitting the control command related to the backup operation or the restoration operation for the wireless probe.

The receiving of the information regarding the operational state of the wireless probe may include receiving the information regarding the operational state of the wireless probe through wireless communication when the operational state of the wireless probe changes.

The transmitting of the control command may include providing information regarding a backed up state of configuration information of the wireless probe when the control command related to the backup operation for the wireless probe is transmitted.

The transmitting of the control command may include providing information regarding a restored state of configuration information of the wireless probe when the control command related to the restoration operation for the wireless probe is transmitted.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION

Figure 1:
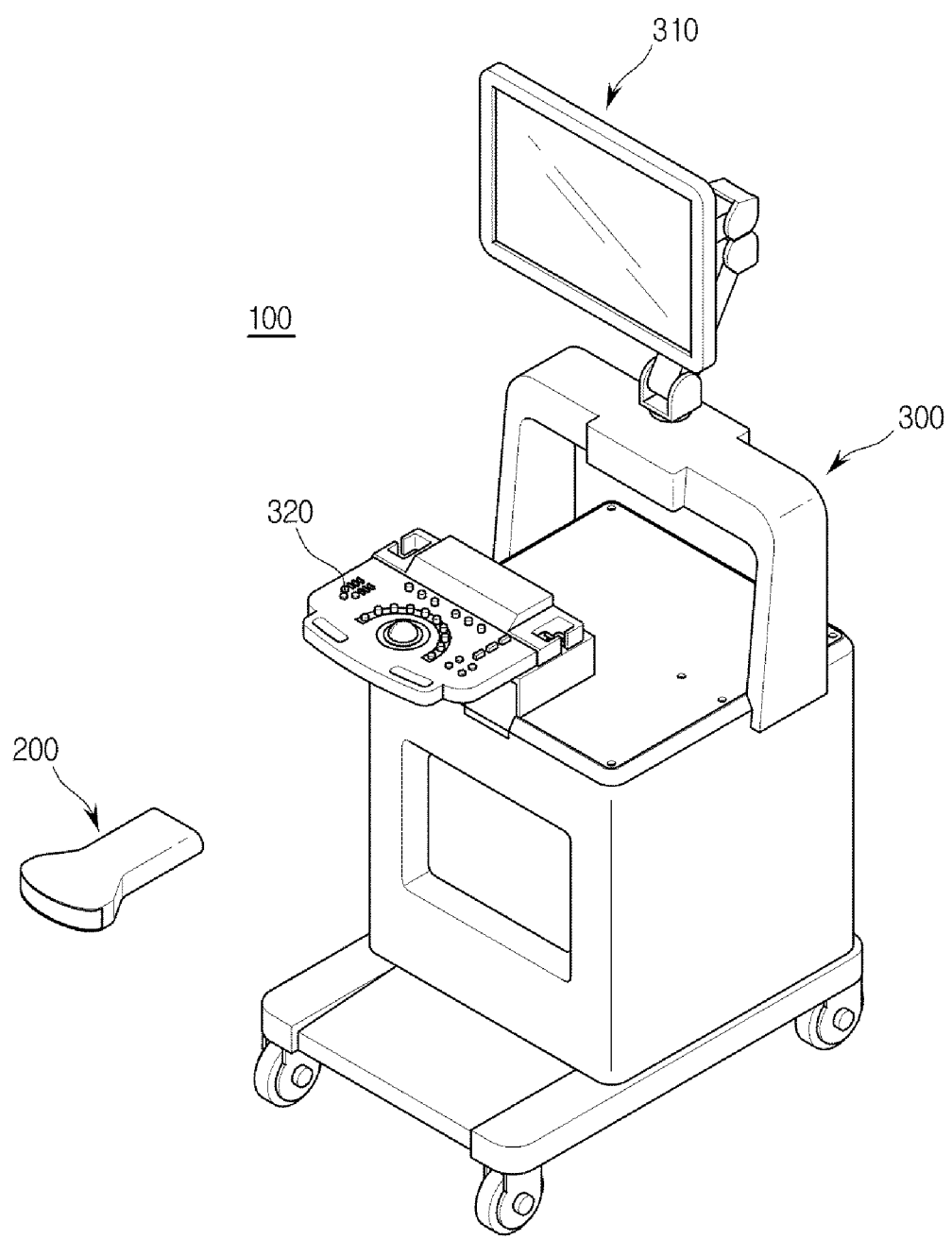
FIG. 1 illustrates the exterior of an ultrasound diagnostic system that includes a wireless probe and an ultrasound diagnostic apparatus in accordance with one embodiment of the present invention.

Reference will now be made in detail to the embodiments of the present invention, examples of which are illustrated in the accompanying drawings, wherein like reference numerals refer to like elements throughout.

FIG. 1 illustrates the exterior of an ultrasound diagnostic system 100 that includes a wireless probe 200 and an ultrasound diagnostic apparatus 300 in accordance with one embodiment of the present invention.

Referring to FIG. 1, the ultrasound diagnostic system 100 includes the wireless probe 200 that transmits ultrasound waves to an object, receives echo ultrasound waves from the object, and transforms the echo ultrasound waves into an electrical signal; and the ultrasound diagnostic apparatus 300 that is connected to the wireless probe 200 via a wireless communication network and displays an ultrasound image.

The wireless probe 200 may be connected to the ultrasound diagnostic apparatus 300 via the wireless communication network so as to receive various signals for controlling the wireless probe 200 or transmit an analog signal or a digital signal corresponding to an ultrasound echo signal received by the wireless probe 200. In addition, the wireless probe 200 may transmit information regarding an operational state thereof to the ultrasound diagnostic apparatus 300 via the wireless communication network.

According to an embodiment of the present invention, the wireless communication network is a communication network via which a signal is exchanged in a wireless manner. However, embodiments of the wireless communication network are not limited thereto and should be understood as including various communication networks via which various signals may be exchanged between the wireless probe 200 and the ultrasound diagnostic apparatus 300.

The ultrasound diagnostic apparatus 300 may include an input unit 320 and a display 310. The input unit 320 may receive configuration information regarding the wireless probe 200, various control commands, etc. from a user. According to an embodiment of the present invention, the configuration information regarding the wireless probe 200 includes gain information, zoom information, focus information, time gain compensation (TGC) information, depth information, frequency information, power information, frame average information, dynamic range information, etc. However, the configuration information regarding the wireless probe 200 is not limited thereto and may include various information that may be set to obtain an ultrasound diagnostic image. The above information may be transmitted to the wireless probe 200 via the wireless communication network, and the wireless probe 200 may be configured based on the transmitted information.

The input unit 320 may be embodied as a keyboard, a foot switch, or a foot pedal. For example, the keyboard may be embodied as hardware. The keyboard may include at least one among a switch, a key, a joy stick, and a track ball. As another example, the keyboard may be embodied as software such as a graphical user interface. In this case, the keyboard may be displayed on the display 310. The foot switch or the foot pedal may be installed at the bottom of the ultrasound diagnostic apparatus 300, and a user may control an operation of the ultrasound diagnostic apparatus 300 using the foot pedal.

The display 310 may display an ultrasound image of a target region of the inside of an object. The ultrasound image displayed on the display 310 may be a two-dimensional (2D) ultrasound image or a three-dimensional (3D) ultrasound image. Various ultrasound images may be displayed according to an operational mode of the ultrasound diagnostic apparatus 300. Also, the display 310 may display not only a menu or a guide for an ultrasound diagnosis but also information regarding an operational state of the wireless probe 200.

The display 310 may be embodied as well-known various display devices such as a cathode ray tube (CRT), a liquid crystal display (LCD), a light-emitting diode (LED), a plasma display panel (PDP), an organic light-emitting diode (OLED), etc.

When the display 310 is a touch screen type, the display 310 may also function as the input unit 320. That is, a user may input various commands to the ultrasound diagnostic apparatus 300 via the display 310 or the input unit 320.

Figure 2:
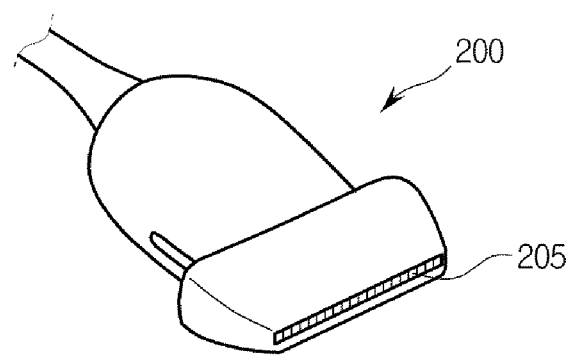
FIG. 2 illustrates the exterior of a wireless probe that includes a one-dimensional (1D) array transducer in accordance with one embodiment of the present invention.
Figure 3:
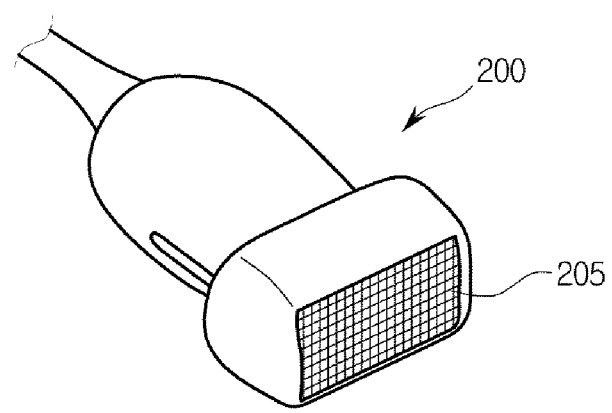
FIG. 3 illustrates the exterior of a wireless probe that includes a two-dimensional (2D) array transducer in accordance with another embodiment of the present invention.

In addition, the ultrasound diagnostic apparatus 300 may include a voice recognition sensor. Thus, a user may input various commands to the ultrasound diagnostic apparatus 300 using voice commands. The structure of the wireless probe 200 will be described in more detail below FIG. 2 illustrates the exterior of a wireless probe 200 that includes a one-dimensional (1D) array transducer in accordance with one embodiment of the present invention. FIG. 3 illustrates the exterior of a wireless probe 200 that includes a 2D array transducer in accordance with another embodiment of the present invention.

The wireless probe 200 may transmit or receive ultrasound waves while in contact with a surface of an object. In detail, the wireless probe 200 may transmit ultrasound waves to the inside of an object according to a transmission signal received from the ultrasound diagnostic apparatus 300, receive echo ultrasound waves reflected from a specific region of the inside of the object, and transmit the echo ultrasound waves to the ultrasound diagnostic apparatus 300. Thus, the wireless probe 200 may transmit the echo ultrasound waves received from the object to the ultrasound diagnostic apparatus 300 via the wireless communication network.

In this case, the wireless probe 200 may include a transducer array that transforms an electrical signal into an ultrasound signal or vice versa to transmit ultrasound waves into the object. The transducer array includes a plurality of transducer elements.

A transducer module 205 which will be described below includes a transducer array. The transducer array includes a plurality of transducer elements. The transducer array may be a 1D array or a 2D array. According to an embodiment of the present invention, the transducer module 205 may include a 1D array transducer as illustrated in FIG. 2. Each of a plurality of transducer elements of the 1D array transducer may transform an electrical signal into an ultrasound signal or vice versa. To this end, each of the plurality of transducer elements may be embodied as a magnetostrictive ultrasound transducer using a magnetostrictive effect of a magnetic substance, a piezoelectric ultrasound transducer using a piezoelectric effect of a piezoelectric material, a piezoelectric micromachined ultrasound transducer (pMUT), etc. Otherwise, each of the plurality of transducer elements may be embodied as a capacitive micromachined ultrasound transducer (cMUT) that transmits or receives ultrasound waves using vibration of several hundreds of or several thousands of micromachined thin films.

In the wireless probe 200, the transducer module 205 may be arranged in a linear form as illustrated in FIG. 2 or may be arranged in a convex form. A basic operational principle of the wireless probe 200 is the same both when the transducer module 205 is arranged in the linear form and when the transducer module 205 is arranged in the convex form. However, in the case of the wireless probe 200 including the transducer module 205 arranged in the convex form, ultrasound waves emitted from the transducer module 205 are fan shaped and thus a generated ultrasound image may also have a fan shape.

As another example, the transducer module 205 may include a 2D array transducer as illustrated in FIG. 3. When the transducer module 205 includes the 2D array transducer, a 3D image of the inside of an object may be obtained.

A plurality of transducer elements of the 2D array transducer are the same as those of the 1D array transducer and will thus not be described in detail here. The relationship between the wireless probe 200 and the ultrasound diagnostic apparatus 300 will be described below.

Figure 4:
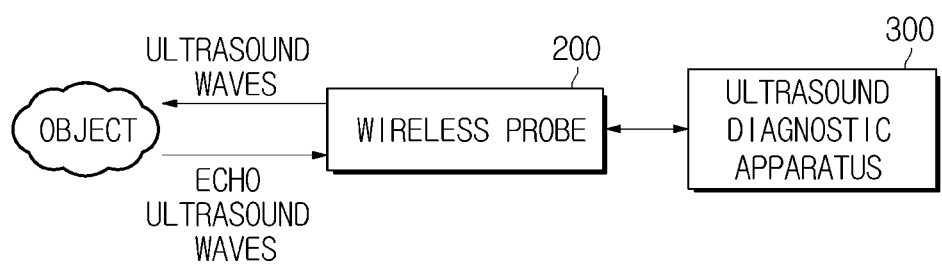
FIG. 4 is a diagram illustrating the relationship between a wireless probe and an ultrasound diagnostic apparatus in accordance with one embodiment of the present invention.

FIG. 4 is a diagram illustrating the relationship between the wireless probe 200 and the ultrasound diagnostic apparatus 300 in accordance with one embodiment of the present invention.

An ultrasound system may include the wireless probe 200 and the ultrasound diagnostic apparatus 300. Referring to FIG. 4, the ultrasound system may irradiate an ultrasound signal toward a target region of the inside of an object, i.e., a body, from a surface of the object using the wireless probe 200, obtain a tomographic image of a soft tissue or an image of a blood flow in a noninvasive manner using information contained in a reflected ultrasound signal (i.e., an ultrasound echo signal), and provide the obtained image to a user. The structure of the wireless probe 200 has been described above and is thus not described again here.

The ultrasound diagnostic apparatus 300 may further include an image processing module that transforms received echo ultrasound waves into an ultrasound image. The image processing module may be embodied as hardware such as a microprocessor or may be embodied as software that may be performed by hardware.

The image processing module may generate an ultrasound image in various modes, e.g., an amplitude mode (A-mode), a brightness mode (B-mode), a motion mode (M-mode), a Doppler mode, etc., and display the ultrasound image on the display 350. When the wireless probe 200 includes either a 2D array transducer or a 1D array transducer that may be driven in an altitude direction, a 3D ultrasound image may be generated from a plurality of 2D cross-sectional images.

A generated ultrasound image may be stored in a memory (not shown) included in the ultrasound diagnostic apparatus 300. In addition, the ultrasound image may be stored in web storage or a cloud server used as storage on the web. The internal structures of the wireless probe 200 and the ultrasound diagnostic apparatus 300 will be described in detail below.

Figure 5:
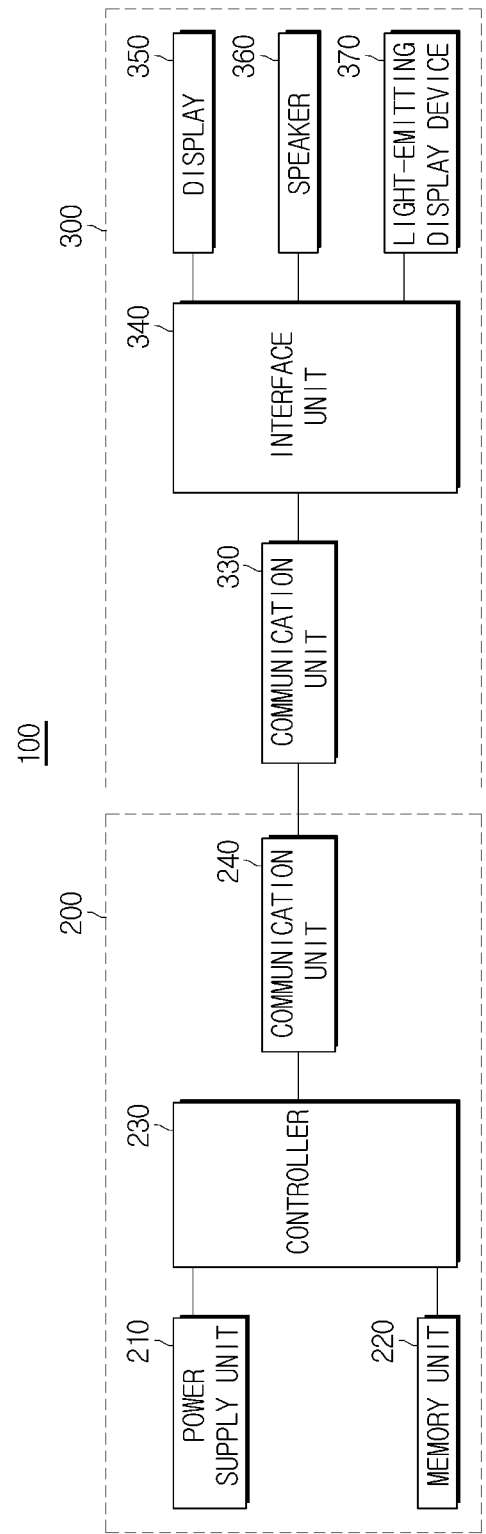
FIG. 5 is a block diagram of a wireless probe and an ultrasound diagnostic apparatus in accordance with one embodiment of the present invention.

FIG. 5 is a block diagram of the wireless probe 200 and the ultrasound diagnostic apparatus 300 in accordance with one embodiment of the present invention.

Referring to FIG. 5, the wireless probe 200 may include a power supply unit 210, a memory unit 220, a controller 230, and a communication unit 240. The components of the wireless probe 200 will be individually described below.

The power supply unit 210 may supply power to the wireless probe 200. In detail, the power supply unit 210 may transform electric energy into chemical energy, accumulate the chemical energy, and supply power by transforming the chemical energy into electric energy. According to an embodiment of the present invention, the power supply unit 210 may be embodied as a lithium ion battery, a nickel metal hydride battery, a polymer battery, etc. However, the power supply unit 210 is not limited thereto and may be embodied as other various batteries that may be included in the wireless probe 200 to supply power.

The power supply unit 210 may be charged according to a wired charging method of directly connecting the power supply unit 210 to a charging device or according to a wireless charging method. That is, the power supply unit 210 may be charged according to well-known various charging methods.

The communication unit 240 may exchange various data with the ultrasound diagnostic apparatus 300 via a wireless communication network. The communication unit 240 may exchange data related to diagnosing an object, e.g., an ultrasound image of an object, echo ultrasound waves, Doppler data, etc., with the ultrasound diagnostic apparatus 300 via the wireless communication network. Also, the communication unit 240 may receive a user's control command from the ultrasound diagnostic apparatus 300 or transmit information regarding an operational state of the wireless probe 200 to the ultrasound diagnostic apparatus 300. That is, the type of data that the communication unit 240 may transmit or receive is not limited.

The communication unit 240 may include at least one component for communicating with an external device. For example, the communication unit 240 may establish wireless communication with the ultrasound diagnostic apparatus 300 using at least one of a local area communication module and a mobile communication module.

The local area communication module means a module for establishing local area communication within a predetermined distance. Examples of local area communication technology may include, but are not limited to, a wireless local area network (LAN), Wi-Fi, Bluetooth, Zigbee, Wi-Fi direct (WFD), ultra wideband (UWB), infrared data association (IrDA), Bluetooth low energy (BLE), near-field communication (NFC), etc.

The mobile communication module may exchange a radio signal with at least one among a base station, an external terminal, and a server in a mobile communication network. Examples of the radio signal may include a voice call signal, a video telephony call signal, various types of data for exchanging a text/multimedia message, etc. That is, the communication unit 240 may exchange various types of data with the ultrasound diagnostic apparatus 300 via at least one among a base station, an external terminal, and a server. For example, the communication unit 240 may be connected to, for example, a third-generation (3G) mobile communication network or a fourth-generation (4G) mobile communication network so as to exchange various types of data with the ultrasound diagnostic apparatus 300 via a base station.

The controller 230 may control overall operations of the wireless probe 200. The controller 230 may be operated by a processor (not shown) included in the wireless probe 200, and may control operations of the power supply unit 210, the memory unit 220, and the communication unit 240 by generating a control signal for controlling these components.

According to an embodiment of the present invention, the controller 230 may determine an operational state of the wireless probe 200. Thus, the controller 230 may determine whether the operational state of the wireless probe 200 is a normal state in which an ultrasound diagnostic image may be captured or an abnormal state in which an ultrasound diagnostic image cannot be captured.

In the present disclosure, the normal state means a state in which an ultrasound diagnostic image may be captured by the wireless probe 200. For example, the normal state means either a state in which the amount of power that may be supplied from the power supply unit 210 to capture an ultrasound diagnostic image is sufficient or a state in which the wireless probe 200 is not switched to an operation stop mode by a user. In addition, the normal state should be understood as including various states in which an ultrasound diagnostic image may be captured by the wireless probe 200, and is not thus limited.

In contrast, the abnormal state means a state in which an ultrasound diagnostic image cannot be captured. For example, the abnormal state should be understood as including a state in which the power supply unit 210 is switched to a maximum power save mode since the amount of power that may be supplied from the power supply unit 210 to capture an ultrasound diagnostic image is not sufficient, a state in which the wireless probe 200 is powered off, a state in which the power supply unit 210 is detached from the wireless probe 200, etc. In addition, the abnormal state may mean a state in which the wireless probe 200 is switched to the operation stop mode by a user so that use of the wireless probe 200 may be stopped. In addition, the abnormal state should be understood as including various states in which an ultrasound diagnostic image cannot be captured by the wireless probe 200, and is not thus limited.

According to an embodiment of the present invention, when an operational state of the wireless probe 200 is switched from the normal state to the abnormal state, the controller 230 may back up configuration information of the wireless probe 200 in the memory unit 220. A backup process means a process of making a copy of original data in preparation for a case in which the original data is damaged, initialized, or deleted. That is, when the wireless probe 200 changes to the abnormal state, information related to the wireless probe 200 that is set by a user may be initialized. Thus, in order to remove the user's inconvenience of resetting the state of the wireless probe 200 due to initialization of the state of the wireless probe 200, the controller 230 may back up, in the memory unit 220, the configuration information of the wireless probe 200 right before the wireless probe 200 changes to the abnormal state.

The configuration information of the wireless probe 200 which will be described below may include various information that may be set to capture an ultrasound diagnostic image. For example, the configuration information of the wireless probe 200 includes at least one among gain information, zoom information, focus information, time gain compensation (TGC) information, depth information, frequency information, power information, frame average information, and dynamic range information of the wireless probe 200.

The configuration information of the wireless probe 200 may further include identification information identifying the ultrasound diagnostic apparatus 300 connected to the wireless probe 200 via a wireless communication network. For example, the identification information includes a host name, an Internet protocol (IP) address, etc. of the ultrasound diagnostic apparatus 300. In addition, the identification information includes various information identifying the ultrasound diagnostic apparatus 300 when the ultrasound diagnostic apparatus 300 and the wireless probe 200 are wirelessly connected. The controller 230 may back up the identification information of the ultrasound diagnostic apparatus 300, so that the wireless probe 200 and the ultrasound diagnostic apparatus 300 may be rapidly connected in a wireless manner when the operational state of the wireless probe 200 changes to the normal state again.

As another example, when the wireless probe 200 is switched from the abnormal state to the normal state, the controller 230 may restore the configuration of the wireless probe 200 based on the configuration information of the wireless probe 200 that has been backed up in the memory unit 220. That is, the controller 230 may reset a state of the wireless probe 200 by bringing the configuration information of the wireless probe 200 stored in the memory unit 220. Thus, even if the wireless probe 200 is suddenly powered off, a user need not input previously set configuration information again.

The controller 230 may determine whether a current state is a backed up state or a restored state and transmit information indicating that the current state is the backed up state or the restored state to the ultrasound diagnostic apparatus 300 via the communication unit 240. Also, after a backup operation or a restoration operation is completed, the controller 230 may determine whether the backup operation or the restoration operation is completed normally, and transmit a result of determining whether the backup operation or the restoration operation is completed normally to the ultrasound diagnostic apparatus 300. Thus, a user may receive information regarding the backed up state or the restored state of the wireless probe 200 from the ultrasound diagnostic apparatus 300.

The controller 230 may manage the power supply unit 210. In detail, the controller 230 may check the amount of power remaining in the power supply unit 210 and determine whether the amount of remaining power is sufficient to capture an ultrasound diagnostic image. Thus, the controller 230 may continuously check the amount of power remaining in the power supply unit 210, and control the power supply unit 210 to be automatically switched to the maximum power save mode or control the communication unit 240 to transmit to a user an inquiry as to whether the power supply unit 210 is to be switched to the maximum power save mode, when it is determined that the amount of remaining power is insufficient to capture an ultrasound diagnostic image.

The memory unit 220 may store the configuration information of the wireless probe 200. The memory unit 220 may be embodied as a small-sized memory included in the wireless probe 200 to store data. According to an embodiment of the present invention, the memory unit 220 may be embodied as a card type memory such as a secure digital (SD) card, a solid state drive (SSD) card, etc. However, the memory unit 220 is not limited thereto and may be embodied as various types of memory included in the wireless probe 200 to store various information.

The wireless probe 200 may include various devices to provide information regarding the wireless probe 200. Information regarding the wireless probe 200 which will be described below should be understood as including various information for determining a state of the wireless probe 200. The information regarding the wireless probe 200 includes information regarding an operational state of the wireless probe 200. For example, the information regarding the operational state of the wireless probe 200 means various information for determining an overall operational state of the wireless probe 200, such as power supply information (e.g., the amount of remaining power of the wireless probe 200, an available time according to the amount of remaining power, etc.), and information indicating whether the wireless probe 200 is in the normal state or the abnormal state. In addition, the information regarding the wireless probe 200 includes a backed up state of the configuration information of the wireless probe 200, a restored state of the configuration information of the wireless probe 200, etc.

For example, although not shown, the wireless probe 200 may include a display or a speaker, so that the wireless probe 200 may display the information regarding the wireless probe 200 on the display or output the information regarding the wireless probe 200 via the speaker to provide a user with the information regarding the wireless probe 200. In this case, the wireless probe 200 may display the information regarding the wireless probe 200 on the display in a popup form.

As another example, the wireless probe 200 may include a light-emitting display device (not shown) to provide the information regarding the wireless probe 200 using the light-emitting display device. In the present disclosure, the term 'light-emitting display device' means a device that emits light using fluorescent materials between electrodes arranged in horizontal and vertical directions. For example, the light-emitting display device may be embodied as a liquid crystal display (LCD), a light-emitting diode (LED), etc. but is not limited thereto.

In the wireless probe 200, the information regarding the wireless probe 200 may be displayed using flickering of the light-emitting display device or using different colors. According to an embodiment of the present invention, the light-emitting display device may emit red light while the wireless probe 200 is being charged, and may emit yellow light while the wireless probe 200 is backed up. When the backup of the wireless probe 200 ends, the light-emitting display device may emit green light.

As another example, the light-emitting display device may flicker in yellow at predetermined time intervals while the wireless probe 200 is backed up, and emit green light when the backup of the wireless probe 200 ends. That is, a user may be provided with the information regarding the wireless probe 200 using the light-emitting display device. A method of providing the information regarding the wireless probe 200 using the light-emitting display device is not, however, limited thereto and information regarding an operational state of the wireless probe 200 may be provided in various ways. Referring to FIG. 5, the ultrasound diagnostic apparatus 300 may include a communication unit 330, an interface unit 340, a display 350, a speaker 360, and a light-emitting display device 370. The communication unit 330, the interface unit 340, the display 350, the speaker 360, and the light-emitting display device 370 may be controlled by a processor included in the ultrasound diagnostic apparatus 300. The components of the ultrasound diagnostic apparatus 300 will be individually described below.

The communication unit 330 may exchange various data with the wireless probe 200 via a wireless communication network. The communication unit 330 may transmit or receive not only data related to diagnosing an object (e.g., an ultrasound image of the object, echo ultrasound waves, Doppler data, etc.) but also medical images captured by other medical apparatuses such as computed tomography (CT), a magnetic resonance imaging (MRI), X-ray, etc. via the wireless communication network. Also, the communication unit 330 may receive various control commands from a user and transmit them to the wireless probe 200. That is, the type of data that the communication unit 330 may transmit and receive is not limited.

Furthermore, the communication unit 330 may receive information regarding an operational state of the wireless probe 200, etc. In the present disclosure, the information regarding the operational state of the wireless probe 200 should be understood as including various information for determining an overall operational state of the wireless probe 200, e.g., the amount of remaining power of the wireless probe 200, an available time according to the amount of remaining power, a configuration state of the wireless probe 200, information indicating whether the wireless probe 200 is in the normal state or the abnormal state, etc. In addition, the information regarding the operational state of the wireless probe 200 includes various information for determining the operational state of the wireless probe 200.

For example, the communication unit 330 may receive the information regarding the operational state of the wireless probe 200 continuously or at predetermined time intervals. Otherwise, the communication unit 330 may receive the information regarding the operational state of the wireless probe 200 only when the operational state of the wireless probe 200 changes. Thus, even if the wireless probe 200 is at a remote place, a user may easily determine the operational state of the wireless probe 200.

In addition, the communication unit 330 may exchange various signals with an external device or a server via the wireless communication network. For example, the communication unit 330 may exchange data with a hospital server or another medical apparatus installed in a hospital to which the communication unit 330 is connected via a picture archiving and communication system (PACS). The communication unit 330 may establish data communication according to standards for digital imaging and communications in medicine (DICOM).

The communication unit 330 may include at least one component for communicating with not only the wireless probe 200 but also another external device. For example, the communication unit 330 may include a local area communication module and a mobile communication module. The local area communication module and the mobile communication module have been described above and are thus not described here again.

The interface unit 340 may provide a user with the information regarding the operational state of the wireless probe 200 so that the user may determine the operational state of the wireless probe 200. For example, the interface unit 340 may display the information regarding the operational state of the wireless probe 200 on the display 350. In this case, the interface unit 340 may display the information regarding the operational state of the wireless probe 200 on the display 350 in a popup form.

As another example, the interface unit 340 may transmit the information regarding the operational state of the wireless probe 200 via the speaker 360. As another example, the ultrasound diagnostic apparatus 300 may include a light-emitting display device 370. Thus, the interface unit 340 may provide the information regarding the operational state of the wireless probe 200 using the light-emitting display device 370. A method of providing the information regarding the operational state of the wireless probe 200 using the light-emitting display device 370 is as described above and is thus not described again here.

In addition, the interface unit 340 may provide a user with information regarding a backed up state, a restoration state, etc. of the configuration information of the wireless probe 200 using at least one among the display 350, the speaker 360, and the light-emitting display device 370.

The interface unit 340 may receive a control command with respect to the wireless probe 200 from a user by transmitting the information regarding the operational state of the wireless probe 200 to the user. For example, the interface unit 340 may receive the user's control command using the display 350 embodied as a touch screen type. Also, the interface unit 340 may receive the user's control command using a microphone (not shown). In addition, referring to FIG. 1, the interface unit 340 may receive the user's control command via the input unit 320 embodied as a foot switch, a foot pedal, a keyboard, or the like.

The control command should be understood as including various commands for controlling the operational state of the wireless probe 200. Examples of the control command include a backup-related control command instructing to back up the configuration information of the wireless probe 200 as the wireless probe 200 changes to the abnormal state, and a restoration-related control command instructing to restore the backed up configuration information of the wireless probe 200 as the wireless probe 200 changes to the normal state.

According to an embodiment of the present invention, when the operational state of the wireless probe 200 changes from the normal state to the abnormal state, a user who receives information regarding the change in the operational state of the wireless probe 200 may input the backup-related control command to the interface unit 340. Thus, the interface unit 340 may receive the backup-related control command and transmit it to the communication unit 330.

As another example, when the operational state of the wireless probe 200 changes from the abnormal state to the normal state, the user who receives information regarding the change in the operational state of the wireless probe 200 may input the restoration-related control command to the interface unit 340. Thus, the interface unit 340 may receive the restoration-related control command and transmit it to the communication unit 330.

Thus, the communication unit 330 may transmit the backup-related control command or the restoration-related control command received from the user to the wireless probe 200, and the wireless probe 200 may perform a backup process or a restoration process based on the received control command.

Figure 6:
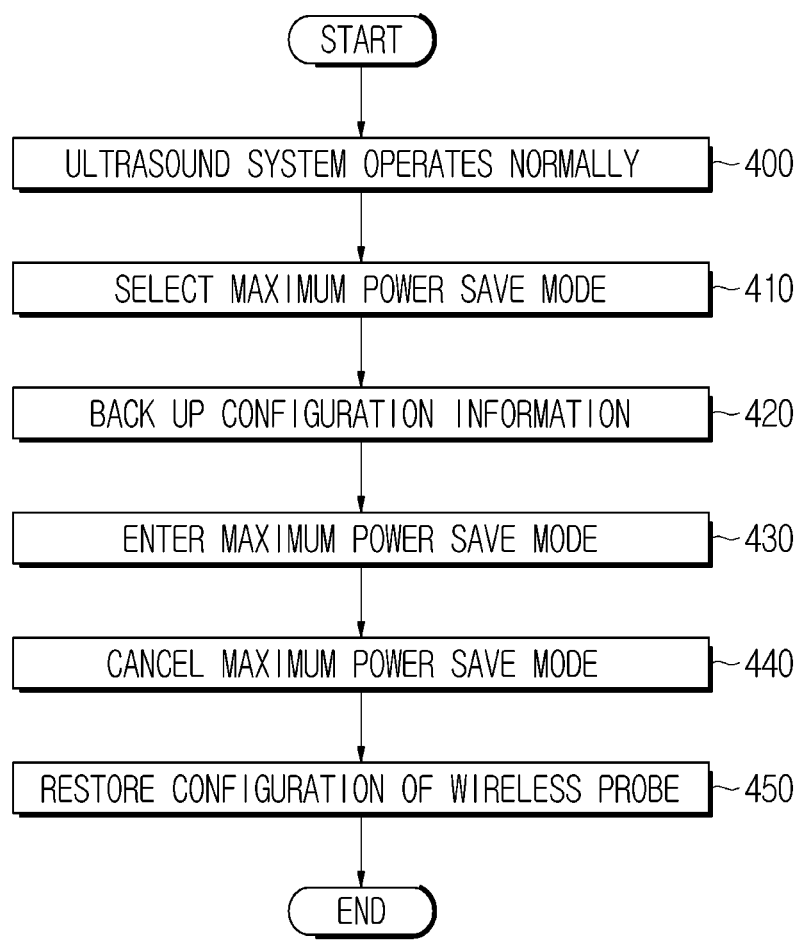
FIG. 6 is a flowchart of an operation of a wireless probe that changes to a maximum power save mode in accordance with one embodiment of the present invention.

FIG. 6 is a flowchart of an operation of a wireless probe that changes to a maximum power save mode in accordance with one embodiment of the present invention.

While an ultrasound system that includes an ultrasound diagnostic apparatus and a wireless probe operates normally (operation S400), the wireless probe may select a maximum power save mode (operation S410). The maximum power save mode means a mode in which although the wireless probe is powered on, the amount of remaining power thereof is nearly zero and thus an ultrasound diagnostic image cannot be captured. When the amount of remaining power of the wireless probe is less than a predetermined reference level, the wireless probe may change to the maximum power save mode. The predetermined reference level may be set by the designer of the ultrasound diagnostic system or a user.

Before entering the maximum power save mode, the wireless probe may back up the configuration information thereof in a memory (operation S420). When entering the maximum power save mode, the wireless probe cannot operate normally. Thus, the configuration information of the wireless probe may be backed up before the wireless probe enters the maximum power save mode, thereby removing inconvenience of resetting the wireless probe after the maximum power save mode is canceled.

When the wireless probe enters the maximum power save mode (operation S430), the wireless probe may not be capable of capturing an ultrasound diagnostic image. In this case, the wireless probe may perform a charging operation. For example, a power supply of the wireless probe may be charged while being directly connected to a charging device according to a wired charging method or may be charged according to a wireless charging method.

When the wireless probe is charged enough to capture an ultrasound diagnostic image and thus the maximum power save mode is canceled (operation S440), the wireless probe may be switched to the normal state in which an ultrasound diagnostic image may be captured. Thus, the wireless probe may restore the backed up configuration information thereof (operation S450). The wireless probe may automatically restore the configuration state thereof based on the backed up configuration information, and thus a user may capture an ultrasound diagnostic image of an object using the wireless probe without resetting the wireless probe.

Otherwise, when the maximum power save mode is canceled, the wireless probe may transmit information indicating a change in the operational state thereof to the ultrasound diagnostic apparatus. When the ultrasound diagnostic apparatus receives a restoration-related control command corresponding to this information from a user, the ultrasound diagnostic apparatus may transmit the restoration-related control command to the wireless probe. Thus, the wireless probe may restore the configuration thereof according to the restoration-related control command. That is, the wireless probe may automatically restore the configuration thereof when the maximum power save mode is canceled or may restore the configuration thereof only when the restoration-related control command is received from a user.

Figure 7:
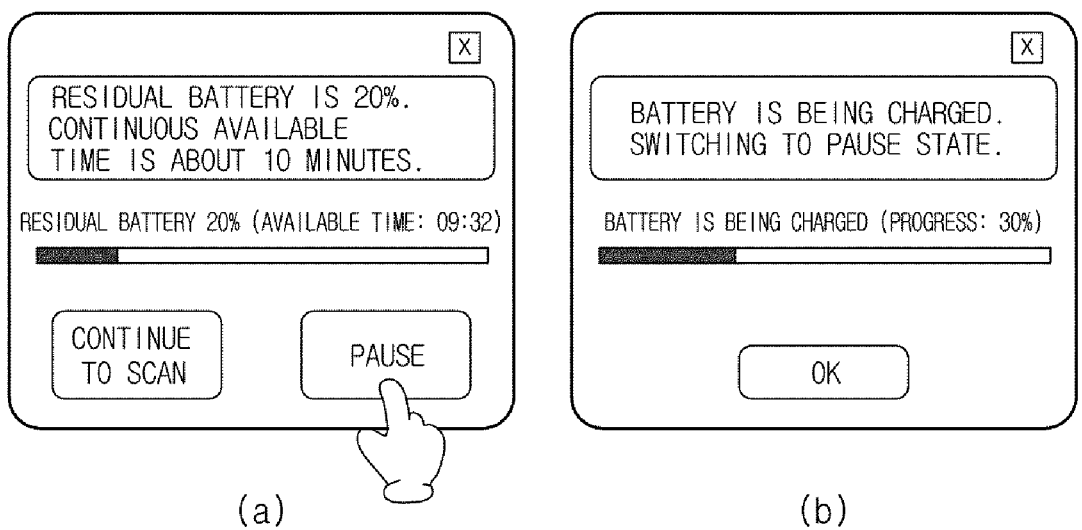
FIG. 7 illustrates screens of an ultrasound diagnostic apparatus that are provided when a wireless probe changes to an operation stop mode in accordance with one embodiment of the present invention.

FIG. 7 illustrates screens of an ultrasound diagnostic apparatus that are provided when a wireless probe changes to an operation stop mode in accordance with one embodiment of the present invention.

The ultrasound diagnostic apparatus may receive information regarding an operational state of the wireless probe from the wireless probe via a wireless communication network. Thus, the ultrasound diagnostic apparatus may display the information regarding the operational state of the wireless probe on a display. Referring to FIG. 7(*a*), the ultrasound diagnostic apparatus may display on the display that a residual battery of the wireless probe is 20% and a continuous available time of the wireless probe is about 10 minutes.

Referring to FIG. 7(*a*), the ultrasound diagnostic apparatus may receive a 'continue to scan' command or a 'pause' command from a user. For example, the ultrasound diagnostic apparatus may receive the 'continue to scan' command or the 'pause' command via an input unit (e.g., a touch screen type display, a voice recognition sensor, a keyboard, a foot pedal, etc.) from the user.

According to an embodiment of the present invention, when the ultrasound diagnostic apparatus receives the 'continue to scan' command from the user, the ultrasound diagnostic apparatus may transmit the 'continue to scan' command to the wireless probe. Thus, the wireless probe may continuously perform scanning or enter a standby state to perform scanning without changing states thereof.

As another example, when the 'pause' command is input to the ultrasound diagnostic apparatus by the user, the ultrasound diagnostic apparatus may transmit the 'pause' command to the wireless probe. Thus, the wireless probe may enter the operation stop mode. In this case, the wireless probe may be switched to the abnormal state in which an ultrasound diagnostic image cannot be captured, i.e., a pause state, and perform a charging operation.

The ultrasound diagnostic apparatus may continuously receive information regarding the operational state of the wireless probe, and display this information on the display. Referring to FIG. 7(*b*), the ultrasound diagnostic apparatus may display a state in which the wireless probe is being charged and a progress of charging the wireless probe.

Figure 8:
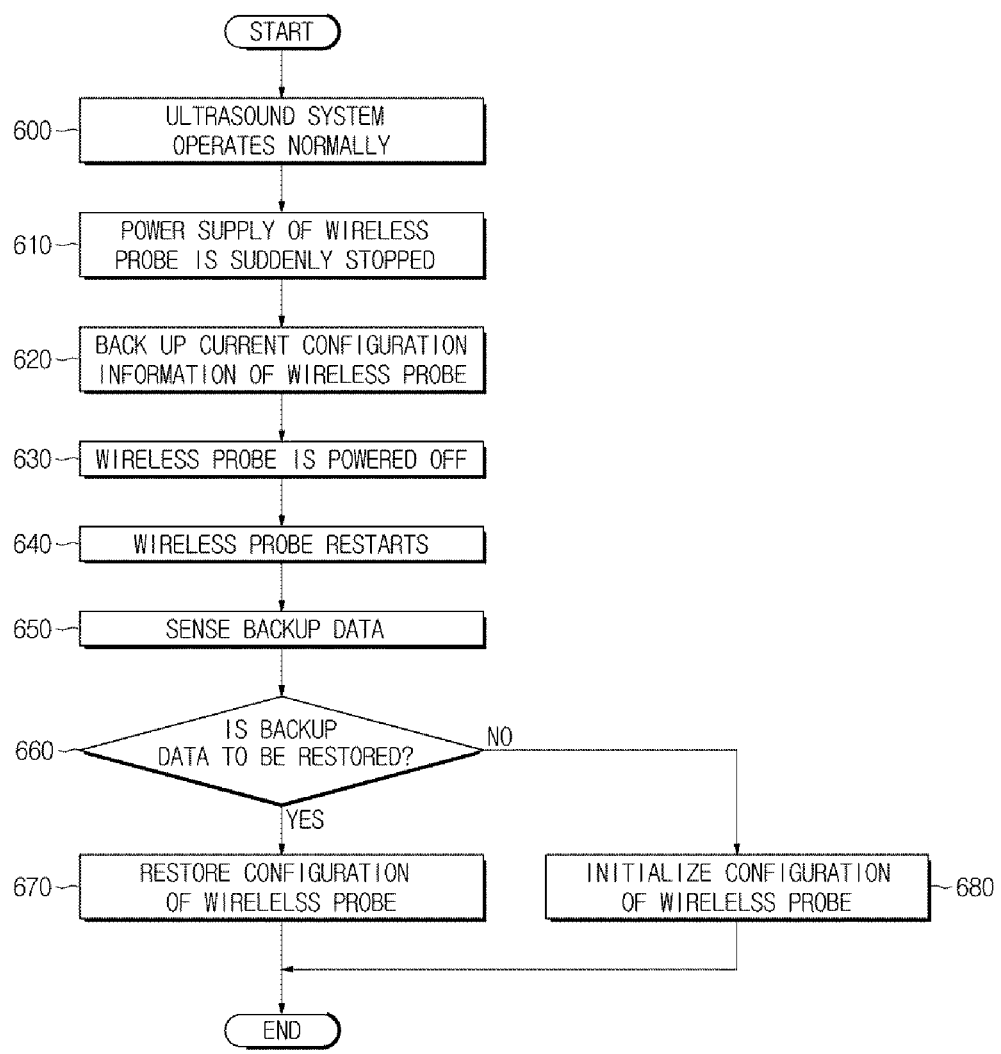
FIG. 8 is a flowchart of an operation of a wireless probe when a power supply of a wireless probe is suddenly stopped in accordance with one embodiment of the present invention.

FIG. 8 is a flowchart of an operation of a wireless probe when a power supply of the wireless probe is suddenly stopped in accordance with one embodiment of the present invention.

While an ultrasound system that includes an ultrasound diagnostic apparatus and a wireless probe operates normally (operation 600), a power supply included in the wireless probe may be suddenly stopped (operation 610). For example, when an external shock is applied to the wireless probe, the power supply may be detached from the wireless probe.

In this case, the wireless probe is not immediately powered off and may be powered on for a short time due to residual power therein. For example, the wireless probe may be powered on for a short time due to electric energy stored in a capacitor included therein. Thus, currently set configuration information of the wireless probe may be backed up in a memory (operation S620). Even if supply of power to the wireless probe is maintained for a short time, the configuration information may be backed up in the memory, since the size of the configuration information is small.

After the backup of the configuration information in the memory is completed, the wireless probe may be powered off (operation S630). When a power supply is installed in the wireless probe and the wireless probe restarts (operation S640), the wireless probe may sense backup data that is backed up in the memory (operation S650). Here, the backup data means the configuration information of the wireless probe that has been backed up in the memory before the wireless probe is powered off.

When the wireless probe senses the backup data, the wireless probe may transmit an inquiry as to whether the backup data is to be restored to a user (operation S660). The wireless probe may be linked to the ultrasound diagnostic apparatus through wireless communication, and transmit the inquiry as to whether the backup data is to be restored to the user via a display or a speaker of the ultrasound diagnostic apparatus. Otherwise, the wireless probe may automatically restore the backup data without transmitting the inquiry as to whether the backup data is to be restored to the user.

When the ultrasound diagnostic apparatus receives a restoration stop command from the user, the wireless probe receives this command from the ultrasound diagnostic apparatus and initializes the configuration of the wireless probe without restoring the backup data (operation S680). Thus, the user has to individually set various states of the wireless probe to capture an ultrasound diagnostic image.

When the ultrasound diagnostic apparatus receives a restoration command from the user, the wireless probe may receive this command from the ultrasound diagnostic apparatus and restore the configuration thereof (operation S670). In this case, the wireless probe may transmit information regarding a restored state of the backup data to the ultrasound diagnostic apparatus through wireless communication. The ultrasound diagnostic apparatus may transmit information regarding the restored state of the backup data to the user via the display or the speaker.

Figure 9:
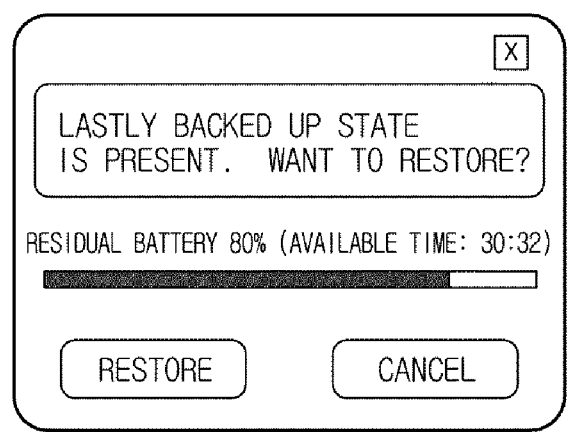
FIG. 9 illustrates a screen for selecting whether configuration of a wireless probe is to be restored when an operational state of the wireless probe changes to a normal state in accordance with one embodiment of the present invention.

FIG. 9 illustrates a screen for selecting whether configuration of a wireless probe is to be restored when an operational state of the wireless probe changes to a normal state in accordance with one embodiment of the present invention.

When the operational state of the wireless probe changes to the abnormal state, configuration information of the wireless probe may be backed up in a memory before the wireless probe enters the abnormal state. Thus, when the wireless probe changes to the normal state, the configuration of the wireless probe may be restored based on the configuration information backed up in the memory. That is, the wireless probe may be restored to the operational state that the wireless probe had while not in the abnormal state.

In this case, the operational state of the wireless probe may be automatically restored based on the configuration information backed up in the memory when the wireless probe changes to the normal state or may be restored only when the restoration command is received from a user. That is, since the user may not want to restore the configuration of the wireless probe, the configuration of the wireless probe may be selectively restored according to the user's command.

When the operational state of the wireless probe changes to the normal state, the wireless probe may transmit information regarding the change in the operational state thereof to the ultrasound diagnostic apparatus via a wireless communication network. Thus, the ultrasound diagnostic apparatus may inquire a user as to whether the operational state of the wireless probe is to be restored to the backed up configuration thereof while providing the user with the information regarding the change in the operational state.

The ultrasound diagnostic apparatus may provide the information regarding the change in the operational state of the wireless probe on the display in a popup form. As illustrated in FIG. 9, the ultrasound diagnostic apparatus may provide a popup form including a residual battery of the wireless probe and information regarding whether the backed up configuration information is to be restored.

In addition, the ultrasound diagnostic apparatus may output the information regarding the change in the operational state of the wireless probe via a speaker. Also, the ultrasound diagnostic apparatus may output the information regarding the change in the operational state of the wireless probe via a light-emitting display device. In addition, the ultrasound diagnostic apparatus may provide information regarding the wireless probe (such as a backed up state and a restored state of the configuration information of the wireless probe) via various devices capable of transmitting information to a user, but is not limited thereto.

Figure 10:
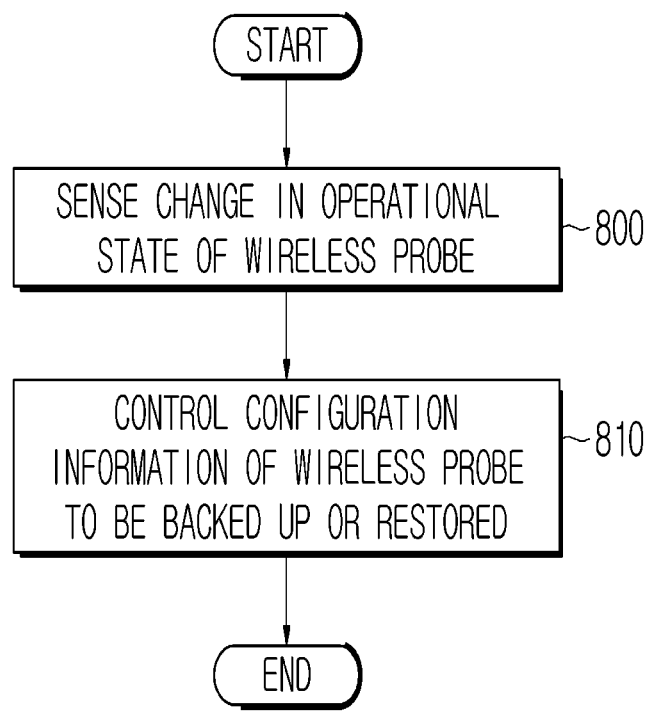
FIG. 10 is a flowchart of a method of controlling a wireless probe by determining a change in an operational state of the wireless probe and backing up or restoring configuration information of the wireless probe in accordance with an embodiment of the present invention.

FIG. 10 is a flowchart of a method of controlling a wireless probe by determining a change in an operational state of the wireless probe and backing up or restoring configuration information of the wireless probe in accordance with an embodiment of the present invention.

The wireless probe may sense a change in an operational state thereof (operation S800). The wireless probe may determine whether the operational state thereof is either the normal state in which an ultrasound diagnostic image may be captured or the abnormal state. For example, the wireless probe may continuously check the amount of power remaining in a power supply thereof to determine whether the wireless probe is in the normal state in which an ultrasound diagnostic image may be captured.

Meanwhile, the wireless probe may transmit information regarding a change in the operational state thereof to the ultrasound diagnostic apparatus through wireless communication. The ultrasound diagnostic apparatus may transmit information regarding the change in the operational state thereof to a user via a display or a speaker. Thus, even if the wireless probe and the ultrasound diagnostic apparatus are not connected via wire such as cable, the user may determine the operational state of the wireless probe via the ultrasound diagnostic apparatus.

The wireless probe may back up configuration information thereof based on the determined change in the operational state thereof or restore configuration thereof based on backed up configuration information thereof (operation S810).

According to an embodiment of the present invention, the wireless probe may determine a change in the operational state thereof, and back up the configuration information thereof in preparation for a case in which the power supply is powered off, based on a result of determining the change in the operational state. In detail, the wireless probe may back up currently set configuration information thereof in the memory when the amount of power remaining in the power supply of the wireless probe is almost zero and thus an ultrasound diagnostic image cannot be captured by the wireless probe and when the power supply is expected to be powered off shortly. Thus, when the wireless probe is switched to the normal state, configuration of the wireless probe may be set based on the configuration information backed up in the memory, thereby increasing a user's convenience.

Figure 11:
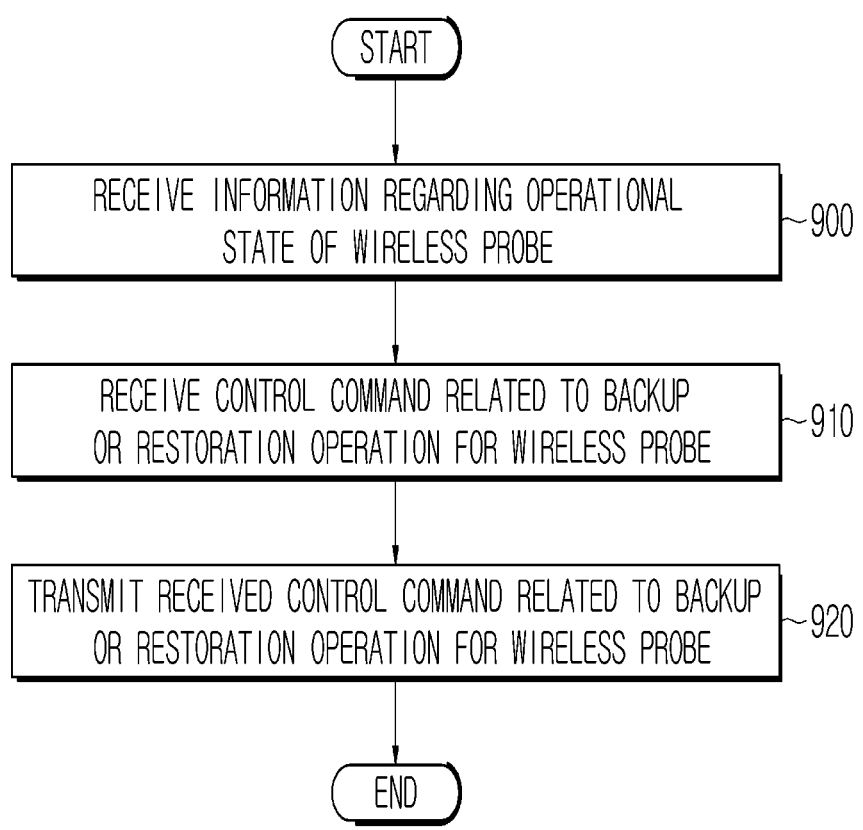
FIG. 11 is a flowchart of a method of controlling an ultrasound diagnostic apparatus to transmit a backup-related control command or a restoration-related control command according to an operational state of a wireless probe in accordance with one embodiment of the present invention.

FIG. 11 is a flowchart of a method of controlling an ultrasound diagnostic apparatus to transmit a backup-related control command or a restoration-related control command according to an operational state of a wireless probe in accordance with one embodiment of the present invention.

The ultrasound diagnostic apparatus may receive information regarding an operational state of a wireless probe via a wireless communication network (operation 900). Thus, the ultrasound diagnostic apparatus may provide a user with information regarding the operational state of the wireless probe.

For example, the ultrasound diagnostic apparatus may display, on a display, information indicating whether an ultrasound diagnostic image is currently being captured by the wireless probe or the wireless probe is in a standby mode. Also, the ultrasound diagnostic apparatus may provide, via the display, information regarding the amount of remaining power or an available time of the wireless probe. In addition, the ultrasound diagnostic apparatus may provide a user with this information via a speaker.

When the operational state of the wireless probe changes, the ultrasound diagnostic apparatus may receive a user's decision as to whether configuration information of the wireless probe is to be backed up or restored while providing the user with information regarding the change in the operational state of the wireless probe (operation 910).

According to an embodiment of the present invention, when the wireless probe changes from the normal state to the abnormal state, the ultrasound diagnostic apparatus may inquire a user as to whether current configuration information of the wireless probe is to be backed up while providing information regarding the change to the user. Thus, the ultrasound diagnostic apparatus may receive a backup-related control command from the user and transmit it to the wireless probe.

As one example, when the backup-related control command is a command instructing to perform a backup operation, the wireless probe may back up the current configuration information thereof in a memory. Thus, whenever the wireless probe changes to the normal state, the configuration of the wireless probe may be restored based on the configuration information backed up in the memory.

As another example, when the backup-related control command is a command instructing to stop the backup operation, the wireless probe may not back up the current configuration information thereof in the memory. Thus, even if the wireless probe changes to the normal state later, the configuration of the wireless probe is not restored to a previous state. Accordingly, the user has to reset the wireless probe to capture an ultrasound diagnostic image.

Meanwhile, the ultrasound diagnostic apparatus may receive information regarding a backed up state of the wireless probe from the wireless probe through wireless communication, and provide a user with this information via the display or the speaker. Thus, the user may determine a progress of a backup operation.

According to another embodiment of the present invention, after the wireless probe changes to the abnormal state and configuration information of the wireless probe is backed up, the wireless probe may change to the normal state, e.g., since a battery of the wireless probe is charged. Thus, the wireless probe may transmit information regarding the change in the operational state thereof to the ultrasound diagnostic apparatus through wireless communication.

Then, the ultrasound diagnostic apparatus may inquire a user as to whether the configuration of the wireless probe is to be restored based on the configuration information while providing the user with the information regarding the change in the operational state via the display or the speaker. Then, the ultrasound diagnostic apparatus may receive a restoration-related control command from the user and transmit this command to the wireless probe (operation 920).

As an example, when the restoration-related control command is a command instructing to perform a restoration operation, the wireless probe may restore the configuration thereof based on current configuration information thereof. As another example, when the restoration-related control command is a command instructing to stop the restoration operation, the wireless probe may be initialized without restoring the configuration of the wireless probe.

Meanwhile, the ultrasound diagnostic apparatus may receive information regarding a restored state of the wireless probe from the wireless probe, and transmit this information to the user. Thus, the user may determine a progress of restoring the wireless probe.

The methods according to the above exemplary embodiments may be embodied as program instructions that may be performed by various computer means, and recorded on a non-transitory computer-readable recording medium. The non-transitory computer-readable recording medium may store program instructions, data files, data structures, or a combination thereof. The program instructions recorded on the recording medium may be designed and configured specially for the exemplary embodiments or may be well-known to those of ordinary skill in the field of computer software. Examples of the non-transitory computer-readable recording medium include magnetic media (e.g., a hard disk, a floppy disk, a magnetic tape, etc.), optical media (e.g., a compact disc (CD)-read-only memory (ROM), a digital versatile disc (DVD), etc.), magneto-optical media (e.g., a floptical disk), and hardware devices specially configured to store and perform program instructions, (e.g., a ROM, a random access memory (RAM), a flash memory, etc.). The program instructions include not only machine language codes prepared by a compiler but also high-level language codes executable by a computer using an interpreter. The hardware device may be configured to operate using at least one software module so as to perform operations according to the exemplary embodiments, and vice versa.

Although a few embodiments of the present invention have been shown and described, it would be appreciated by those skilled in the art that changes may be made in these embodiments without departing from the principles and spirit of the invention, the scope of which is defined in the claims and their equivalents. For example, desired effects of the present invention may be achieved even when the above methods may be performed in orders different from the orders described above and/or the above components such as systems, structures, devices, circuits, etc. may be combined in forms different from the forms described above or replaced with other components or equivalents thereof.

Accordingly, other embodiments or equivalents thereof should be considered to be within the spirit and scope of the invention as defined by the appended claims.

What is claimed is:

1. A wireless probe comprising:
   a power supply unit disposed in the wireless probe to supply power to the wireless probe;
   a memory disposed in the wireless probe to store configuration information of the wireless probe; and
   a controller configured to determine an operational state of the wireless probe and to control the configuration information to be backed up or restored based on the operation state of the wireless probe,
   wherein the operational state of the wireless probe comprises a normal state and an abnormal state, wherein the controller is configured to back up the configuration information in the memory when the operational state of the wireless probe is switched from the normal state to the abnormal state, and
wherein the controller is further configured to restore a configuration of the wireless probe based on the configuration information that has been backed up in the memory when the operational state of the wireless probe is switched from the abnormal state to the normal state,
wherein the abnormal state includes a state in which the controller controls the power supply unit to be switched to a maximum power save mode when an amount of power supplied from the power supply unit is not sufficient to capture an ultrasound diagnostic image, and
wherein the maximum power save mode is a state in which the amount of remaining power of the wireless probe is less than a predetermined reference level.

2. The wireless probe according to claim 1, wherein, in a case in which the operational state of the wireless probe changes from the normal state to the abnormal state, the controller backs up the configuration information in the memory, wherein the ultrasound diagnostic image is obtained in the normal state and is not obtained in the abnormal state.

3. The wireless probe according to claim 2, wherein the case in which the operational state of the wireless probe changes from the normal state to the abnormal state comprises at least one of: a case in which the power supply unit is detached from the wireless probe, a case in which the power supply unit is discharged, a case in which the wireless probe enters the maximum power save mode, or a case in which the wireless probe enters an operation stop mode in which use of the wireless probe is stopped by a user.

4. The wireless probe according to claim 2, wherein the controller determines whether the configuration information is backed up normally in the memory.

5. The wireless probe according to claim 1, further comprising a communication unit to support wireless communication to be established between the wireless probe and an ultrasound diagnostic apparatus.

6. The wireless probe according to claim 1, wherein the configuration information comprises at least one selected from the group consisting of gain information, zoom information, focus information, time gain compensation (TGC) information, depth information, frequency information, power information, frame average information, and dynamic range information of the wireless probe.

7. The wireless probe according to claim 1, wherein the controller determines whether the configuration of the wireless probe is restored based on the configuration information that is backed up in the memory.

8. The wireless probe according to claim 1, further comprising a display to display at least one of: information regarding the operational state of the wireless probe, information regarding a backed up state of the configuration information, or information regarding a restored state of the configuration information.

9. The wireless probe according to claim 1, further comprising a speaker to output at least one of: information regarding the operational state of the wireless probe, information regarding a backed up state of the configuration information, or information regarding a restored state of the configuration information.

10. The wireless probe according to claim 1, further comprising a light-emitting display device to display at least one of: information regarding the operational state of the wireless probe, information regarding a backed up state of the configuration information, or information regarding a restored state of the configuration information.

11. A method of controlling a wireless probe, the method comprising:
determining a change in an operating state of the wireless probe based on a power state of the wireless probe;
controlling configuration information of the wireless probe to be backed up or restored, based on the change in the operational state of the wireless probe;
controlling the wireless probe to back up the configuration information in a memory when the operational state of the wireless probe is switched from a normal state to an abnormal state; and
controlling the wireless probe to restore a configuration of the wireless probe based on the configuration information that has been backed up in the memory when the wireless probe is switched from the abnormal state to the normal state,
wherein the abnormal state includes a state in which a controller of the wireless probe controls a power supply unit of the wireless probe to be switched to a maximum power save mode when an amount of power supplied from the power supply unit is not sufficient to capture an ultrasound diagnostic image, and
wherein the maximum power save mode is a state in which the amount of remaining power of the wireless probe is less than a predetermined reference level.

12. The method according to claim 11, wherein the determining of the change in the operational state of the wireless probe comprises determining whether the wireless probe changes from the normal state to the abnormal state or changes from the abnormal state to the normal state,
wherein the ultrasound diagnostic image is obtained in the normal state and is not obtained in the abnormal state.

13. The method according to claim 11, wherein the controlling configuration information of the wireless probe comprises backing up the configuration information in the memory when it is determined that the operational state of the wireless probe changes from the normal state to the abnormal state.

14. The method according to claim 11, wherein the configuration information comprises at least one selected from the group consisting of gain information, zoom information, focus information, time gain compensation (TGC) information, depth information, and dynamic range information of the wireless probe.

* * * * *